US012042119B2

(12) United States Patent
Ming et al.

(10) Patent No.: US 12,042,119 B2
(45) Date of Patent: Jul. 23, 2024

(54) CONTROL METHOD AND CONTROL SYSTEM FOR CAPSULE ENDOSCOPE (71) Applicant: ANKON TECHNOLOGIES CO., LTD, Wuhan (CN)

(72) Inventors: Fanhua Ming, Wuhan (CN); Tianyi Yangdai, Wuhan (CN); Hangyu Peng, Wuhan (CN); Yanli Liu, Wuhan (CN); Hao Liu, Wuhan (CN)

(73) Assignee: ANKON TECHNOLOGIES CO., LTD., Wuhan (CN)

( * ) Notice: Subject to any disclaimer, the term of this patent is extended or adjusted under 35 U.S.C. 154(b) by 310 days.

(21) Appl. No.: 17/019,245

(22) Filed: Sep. 12, 2020

(65) Prior Publication Data
US 2021/0076916 A1 Mar. 18, 2021

(30) Foreign Application Priority Data
Sep. 12, 2019 (CN) .......................... 201910865561.0

(51) Int. Cl.
A61B 1/00 (2006.01)
A61B 1/04 (2006.01)
A61B 1/045 (2006.01)

(52) U.S. Cl.
CPC ...... A61B 1/00006 (2013.01); A61B 1/00009 (2013.01); A61B 1/041 (2013.01);
(Continued)

(58) Field of Classification Search
CPC ..... A61B 1/041; A61B 1/00009; A61B 1/045; A61B 2562/0219; A61B 2562/0247;
(Continued)

(56) References Cited

U.S. PATENT DOCUMENTS 10,349,820 B2* 7/2019 Schentag ................. A61B 5/07
2008/0080446 A1* 4/2008 Chung ................... H04B 7/082
370/342

(Continued)

FOREIGN PATENT DOCUMENTS

CN 1647749 A 8/2005
CN 1709196 A 12/2005
(Continued)

OTHER PUBLICATIONS

Bo Zhou, et al. Biomedical Electronics Systems: Energy Harvesting and Wireless Data Transmission. Beijing Institute of Technology Press. Jun. 2015, pp. 5-7.

Primary Examiner — Anh Tuan T Nguyen
Assistant Examiner — Shankar Raj Ghimire
(74) Attorney, Agent, or Firm — Treasure IP Group, LLC (57) ABSTRACT A control method and a control system for a capsule endoscope are provided. The control method comprises acquiring a frame rate of the capsule endoscope. The frame rate is the number of frames of images captured by the capsule endoscope per unit time. The control method further comprises controlling the number of radio frequency transmission channels that are turned on according to the frame rate. The number of radio frequency transmission channels that are turned on is at least two, and the radio frequency transmission channels transmit the captured images. The control method and control system for the capsule endoscope can adaptively distribute a plurality of radio frequency transmission channels according to the real-time position of the capsule endoscope, and further turn on the radio frequency transmission channels to transmit a plurality of signals synchronously or asynchronously.

14 Claims, 3 Drawing Sheets (52) U.S. Cl.
CPC ...... *A61B 1/045* (2013.01); *A61B 2562/0219* (2013.01); *A61B 2562/0247* (2013.01); *A61B 2562/0271* (2013.01)

(58) Field of Classification Search
CPC ........ A61B 2562/0271; A61B 1/00158; A61B 1/00016; A61B 1/00006; A61B 1/00131; A61B 1/2736; A61B 1/31; A61B 5/07; A61B 1/00181; A61B 1/0638; A61B 1/000096; A61B 1/0684; A61B 1/000094; A61B 1/0655; H01Q 3/40; H01Q 1/246; H01Q 3/26; H04W 16/28; H04B 7/0814; H04B 7/0822
See application file for complete search history.

(56) References Cited

U.S. PATENT DOCUMENTS

| | | | | |
|---|---|---|---|---|
| 2008/0242926 A1* | 10/2008 | Nishino | ................ | A61B 1/041 600/117 |
| 2008/0249360 A1* | 10/2008 | Li | ....................... | A61B 5/0031 600/109 |
| 2008/0312504 A1* | 12/2008 | Kimoto | ................ | A61B 5/0031 600/118 |
| 2013/0237774 A1* | 9/2013 | Schentag | ........... | A61B 5/14507 600/301 |
| 2016/0213235 A1* | 7/2016 | Hasegawa | ............... | A61B 5/061 |
| 2018/0199800 A1* | 7/2018 | Godo | .................... | A61B 5/067 |
| 2020/0213635 A1* | 7/2020 | Baick | ................... | H04N 21/238 |

FOREIGN PATENT DOCUMENTS

| | | |
|---|---|---|
| CN | 2902187 Y | 5/2007 |
| CN | 102148761 A | 8/2011 |
| CN | 103908216 A | 7/2014 |
| CN | 207150618 U | 3/2018 |
| CN | 109480746 A | 3/2019 |
| CN | 201610552999 A | 4/2019 |

* cited by examiner

CONTROL METHOD AND CONTROL SYSTEM FOR CAPSULE ENDOSCOPE

CROSS-REFERENCE OF RELATED APPLICATIONS

The application claims priority to Chinese Patent Application No. 201910865561.0 filed on Sep. 12, 2019, the contents of which are incorporated by reference herein.

FIELD OF INVENTION

The present invention relates to the art of capsule devices to be used in medical related applications, and more particularly to a control method and a control system for capsule endoscope based on a plurality of radio frequency modules.

BACKGROUND

Capsule endoscope is a medical device. It integrates the core components such as a camera and a wireless transmission antenna into a capsule that can be swallowed by a subject. During examination, the capsule endoscope is swallowed into the subject, then takes images in the digestive tract and transmits the images to the outside of the subject for review and evaluation by a physician.

Due to the characteristics of the parts of digestive tract, the wireless capsule endoscope needs to work in different modes to achieve the optimal working state when in different parts of the digestive tract. For example, the capsule endoscope passes rapidly through the esophagus to the stomach, so the frame rate of the capsule endoscope should be increased to avoid missing information in the esophagus. When the capsule endoscope is in the stomach, it has a high degree of freedom due to a large cavity, so to ensure a complete and efficient examination, it should be controlled flexibly and accurately. Usually, a magnetic control technique is used to control the position and orientation of the capsule endoscope, while a high frame rate is maintained to take images. When the capsule endoscope is in the small intestine, it is restricted in movement and has a relatively low average speed, long operating time, and small ability of intervention by external control, and for a long period time, the capsule endoscope may be relatively stationary with the human body. So, in this part, frame rate of the capsule endoscope should be adaptively adjusted. That is, when the capsule endoscope is moving relative to the human body or the image changes significantly, increase the frame rate, and when it is in a stationary state, reduce the frame rate to save energy. When the capsule endoscope is in the large intestine, the degree of freedom gets higher due to a larger cavity. Therefore, the frame rate should also be adaptively adjusted, same as in the small intestine. In addition, magnetic control technique is also needed to improve the detection efficiency.

In the process of working, the capsule endoscope needs to have a data interaction with the data recorder outside the subject, that is, the working parameters obtained in the subject are transmitted to the data recorder through a radio frequency (radio frequency) module. The working parameters include: parameters obtained by an image sensor and other sensors, wherein the image sensor is used to obtain images, and other sensors are used to obtain the digestive tract parameters and the state parameters of the capsule endoscope, such as pH, cavity pressure, temperature, inertial measurement unit (IMU) data (gyro acceleration, accelerometer acceleration), magnetic field intensity, time-of-flight (TOF) ranging information, ultrasonic echo information, etc. Of the above working parameters, some have a faster signal transmission rate and require real-time high-speed interaction with an external receiving unit. For example, in a capsule endoscope system with location and magnetic-controlled suspension capabilities, magnetic field signals need to be transmitted in real time for an external computing module to calculate the position of the capsule endoscope as the feedback for an external magnetic control system, and the transmission frequency of magnetic field signals can be as high as several kilohertz, which is much higher than the image transmission frame rate.

However, in the prior art, only one RF module is provided in the capsule endoscope, and all the working parameters described above realize interaction with external units through the same channel of the RF module. However, the throughput rate of a single RF module is limited. So, when the frame rate increases, the image size becomes larger, or when the images and magnetic field signals need to be transmitted at the same time, a single RF module in the prior art cannot meet the need.

SUMMARY OF THE INVENTION

The present invention discloses a control method and a control system for a capsule endoscope based on a plurality of radio frequency modules.

To achieve one of the objects of the present invention, there is provided a control method for a capsule endoscope in an embodiment. The method comprises: step S1, acquiring a frame rate of the capsule endoscope, wherein the frame rate is the number of frames of images captured by the capsule endoscope per unit time;

step S2, controlling the number of radio frequency transmission channels that are turned on according to the frame rate, wherein the number of radio frequency transmission channels that are turned on is at least two, and the radio frequency transmission channels transmit the captured images.

In an embodiment of the present invention, step S2 specifically comprises:

controlling to turn on at least two radio frequency transmission channels when the frame rate is greater than a system preset frame rate;

cross-distributing the captured images to the radio frequency transmission channels that are turned on for synchronous or asynchronous output.

In an embodiment of the present invention, step S1 further comprises: collecting location parameters of the capsule endoscope, where the location parameters are magnetic field signals collected by the capsule endoscope in real time;

step S2 further comprises: controlling the number of radio frequency transmission channels that are turned on according to the frame rate and location parameters, wherein the radio frequency transmission channels transmit the location parameters.

In an embodiment of the present invention, step S2 specifically comprises:

controlling to turn on at least two radio frequency transmission channels when the collected location parameters are not empty;

distributing the captured images and location parameters for synchronous or asynchronous output to different radio frequency transmission channels that are turned on.

In an embodiment of the present invention, step S2 specifically comprises:
controlling to turn on at least three radio frequency transmission channels when the collected location parameters are not empty and the frame rate is greater than a system preset frame rate;
distributing the collected location parameters to one of the radio frequency transmission channels for output;
cross-distributing the captured images to at least two other radio frequency transmission channels for synchronous or asynchronous output.

In an embodiment of the present invention, step S1 specifically comprises:
identifying the frame rate of the capsule endoscope, and/or determining whether the collected location parameters are empty according to the current position information of the capsule endoscope.

In an embodiment of the present invention, the RF transmission channels are also used for transmission of control parameters;
step S1 also comprises: collecting control parameters of the capsule endoscope, wherein the control parameters are working parameters obtained by at least one of an acceleration sensor, a gyroscope, a pH sensor, a pressure sensor and a temperature sensor;
step S2 also comprises: distributing the captured images and at least one control parameter to different radio frequency transmission channels that are turned on for synchronous or asynchronous output when the collected control parameters are not empty.

In an embodiment of the present invention, the method further comprises:
turning on a Bluetooth module of the capsule endoscope to broadcast information after the capsule endoscope finishes working, wherein the broadcast information comprises an unique identification number of the current capsule endoscope;
determining whether the capsule endoscope is in a preset position according to the broadcast information.

To achieve another of the objects of the present invention, a control system for the capsule endoscope is provided in an embodiment. The system comprises: an acquisition module for acquiring a frame rate of the capsule endoscope, wherein the frame rate is the number of frames of images captured by the capsule endoscope per unit time;
a control module for controlling the number of radio frequency transmission channels that are turned on according to the frame rate, wherein the number of radio frequency transmission channels that are turned on is at least two, and the radio frequency transmission channels transmit the captured images.

In an embodiment of the present invention, the control module is specifically configured to:
control to turn on at least two radio frequency transmission channels when the frame rate is greater than a system preset frame rate;
cross-distribute the captured images to the radio frequency transmission channels that are turned on for synchronous or asynchronous output.

In an embodiment of the present invention, the acquisition module is also configured to: collect location parameters of the capsule endoscope, wherein the location parameters are magnetic field signals collected by the capsule endoscope in real time;
the control module is also configured to: control the number of radio frequency transmission channels that are turned on according to the frame rate and location parameters, wherein the radio frequency transmission channels transmit the location parameters.

In an embodiment of the present invention, the control module is also configured to: control to turn on at least two radio frequency transmission channels when the collected location parameters are not empty;
distribute the captured images and location parameters for synchronous or asynchronous output to different radio frequency transmission channels that are turned on.

In an embodiment of the present invention, the control module is specifically configured to: control to turn on at least three radio frequency transmission channels when the collected location parameters are not empty and the frame rate is greater than a system preset frame rate;
distribute the collected location parameters to one of the radio frequency transmission channels for output;
cross-distribute the captured images to at least two other radio frequency transmission channels for synchronous or asynchronous output.

In an embodiment of the present invention, the acquisition module is also configured to: identify the frame rate of the capsule endoscope, and/or determine whether the collected location parameters are empty according to the current position information of the capsule endoscope.

In an embodiment of the present invention, the radio frequency transmission channels transmit control parameters;
the acquisition module is configured to collect control parameters of the capsule endoscope, wherein the control parameters are working parameters obtained by at least one of an acceleration sensor, a gyroscope, a pH sensor, a pressure sensor, and a temperature sensor;
the control module is configured to distribute the captured images and at least one control parameter to different radio frequency transmission channels that are turned on for synchronous or asynchronous output when the collected control parameters are not empty.

In an embodiment of the present invention, the control module is also configured to: turn on a Bluetooth module of the capsule endoscope to broadcast information after the capsule endoscope finishes working, wherein the broadcast information comprises an unique identification number of the current capsule endoscope;
determine whether the capsule endoscope is in a preset position according to the broadcast information.

Compared with the prior art, the control method and control system for the capsule endoscope disclosed in the present invention can adaptively distribute a plurality of radio frequency transmission channels according to the real-time position of the capsule endoscope, and further turn on the radio frequency transmission channels to transmit a plurality of signals synchronously or asynchronously, so that the detection requirements can be met and also the energy consumption can be saved.

DETAILED DESCRIPTION

The present invention can be described in detail below with reference to the accompanying drawings and preferred embodiments. However, the embodiments are not intended to limit the invention, and the structural, method, or functional changes made by those skilled in the art in accordance with the embodiments are included in the scope of the present invention.

A capsule endoscope refers to a capsule-shaped device that can be swallowed into a subject. The capsule endoscope comprises a biocompatible enclosure, an image collection unit, a plurality of sensors, a first microcontroller unit (MCU), a first radio frequency (RF) module, a battery and a magnet. The plurality of sensors comprise a magnetic field sensor, an inertial measurement unit (IMU) sensor, a pH sensor, a pressure sensor and a temperature sensor. The magnetic field sensor can be a Hall sensor, an anisotropic magneto resistance (AMR) sensor, a giant magneto resistance (GMR) sensor, or a tunneling magneto resistance (TMR) sensor. The IMU sensor can be an accelerometer or a gyroscope.

The capsule endoscope communicates with an external device. The external device is typically a portable data recorder worn on the subject which wirelessly receives and stores the information sent by the capsule endoscope, while executing the sending and receiving of various instructions. The data recorder comprises a second MCU, a battery, a second RF module, a display device for corresponding sensor, a storage unit, and an antenna system connected to the storage unit. The sensor is mainly an IMU sensor. The data recorder can be connected to an external workstation, such as a server, a personal computer, or a display device, via USB. The workstation is installed with an operating software that can be used to display images captured by the capsule endoscope and various sensor information, perform complex calculations, and control the operating status of the capsule endoscope. Among them, the first RF module in the capsule endoscope and the second RF module in the data recorder exchange data with each other.

Figure 1:
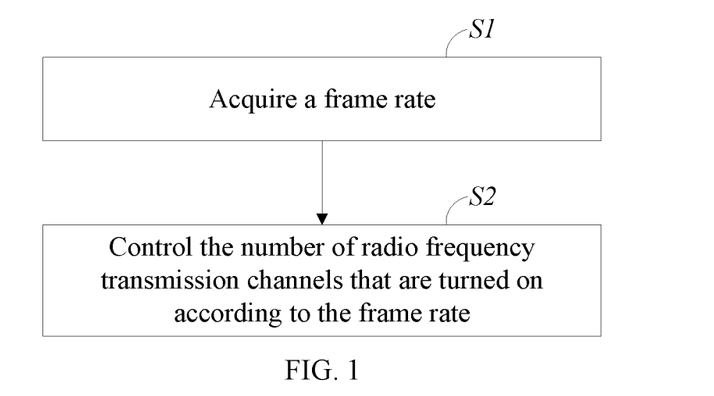
FIG. 1 is a flowchart of a control method for a capsule endoscope according to a first embodiment of the present invention.

As shown in FIG. 1, in a first embodiment of the present invention, a control method for the capsule endoscope is provided. The method comprises: step S1, acquiring a frame rate of the capsule endoscope, where the frame rate is the number of frames of images captured by the capsule endoscope per unit time; step S2, controlling the number of RF transmission channels that are turned on according to the frame rate, wherein the number of RF transmission channels is set to at least two, and the RF transmission channels are used for transmission of the captured images.

In a preferred embodiment of the present invention, the frame rate of the capsule endoscope is identified according to the current position information of the capsule endoscope.

In the specific embodiments of the present invention, the capsule endoscope is located in the digestive tract of the subject, and the frame rate can be adaptively changed according to the position of the capsule endoscope. For example, as described in the background of the invention, when the capsule endoscope is in the esophagus and stomach, the frame rate is relatively high, and when the capsule endoscope is in the small intestine and large intestine, the frame rate can be adaptively adjusted. In the specific embodiments of the present invention, when the capsule endoscope is in any part of the digestive tract, the value of the frame rate is usually preset, and when it is identified that the capsule endoscope is in a certain part of the digestive tract, the frame rate can be adaptively adjusted according to the preset value.

The current position information of the capsule endoscope can be determined in a variety of ways. For example, the feedback images are analyzed to determine the digestive tract part where the capsule endoscope is located. Also, it can be determined by the method disclosed in the Chinese Patent Application No. 201610552999.X, which is not further described herein.

Figure 2:
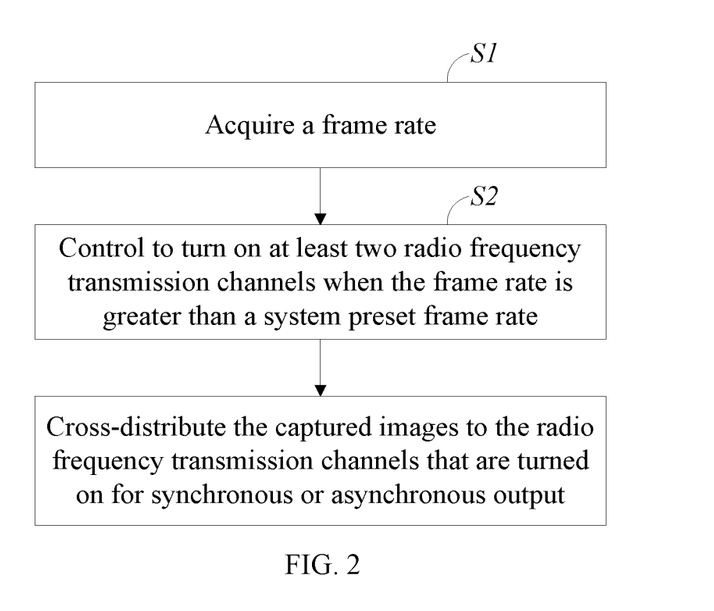
FIG. 2 is a flowchart of a preferred embodiment corresponding to FIG. 1.

As shown in FIG. 2, for step S2, the method specifically comprises: if the frame rate is greater than a system preset frame rate, controlling to turn on at least two RF transmission channels; cross-distributing the captured images to the RF transmission channels that are turned on for synchronous or asynchronous output.

The system preset frame rate is a fixed value, which can be specifically adjusted according to the actual frequency of captured images in each part of the digestive tract as required.

Figure 3:
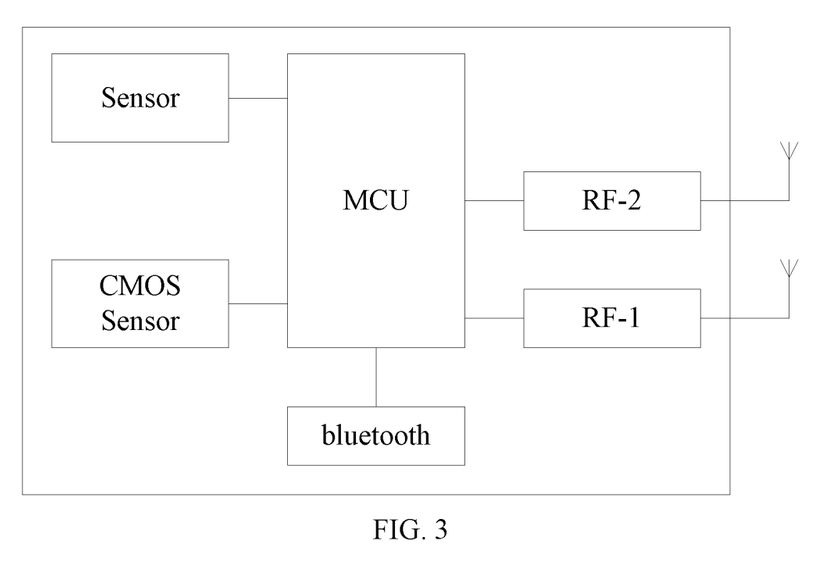
FIG. 3 is a block diagram showing the hardware structure of the capsule endoscope in an specific example of the present invention.

As shown in FIG. 3, in a specific example of the present invention, the capsule endoscope is provided with two RF modules. Each of the RF modules corresponds to a radio frequency transmission channel and is connected to the MCU. Each RF module can be independently set to be in the same frequency band, and can also be set to be in different frequency bands to ensure that there can be no data confusion between them.

Accordingly, the data recorder outside the subject is equipped with the same quantity of RF modules to configure one-to-one with each RF module in the capsule endoscope for data interaction. In addition, the data recorder can also be equipped with an artificial Intelligence (AI) chip or a compute stick for improvement of computing power to support complex machine learning algorithms and realize image-based lesion identification and digestive tract location determination. The implementation of specific functions and specific data processing methods are all existing technologies, and cannot be further described here.

For step S2, the capsule endoscope in the esophagus is taken as an example for detailed introduction, where the system preset frame rate is preset to 20 fps. In the esophagus, for example, if the frame rate of the capsule endoscope is 30 fps, which is greater than the system preset frame rate, both RF transmission channels need to be turned on, that is, both two RF modules are turned on. At this point, the captured images are cross-distributed to the RF transmission channels that are turned on for synchronous or asynchronous output. For example, the images captured per second are sorted in the order as 1, 2, 3 . . . 29, 30. The two RF modules correspond to two RF transmission channels, and the two RF transmission channels are a first RF transmission channel RF-1 and a second RF transmission channel RF-2. Then, the images with odd number are assigned to the first RF transmission channel RF-1 for transmission, and the images with even number are assigned to the second RF transmission channel RF-2 for transmission. In this way, the capsule endoscope has a significantly improved efficiency in data throughput over the traditional one with single RF module.

In practical applications, according to different application conditions, the types of data interacted between the capsule endoscope and the data recorder can also change accordingly.

Figure 4:
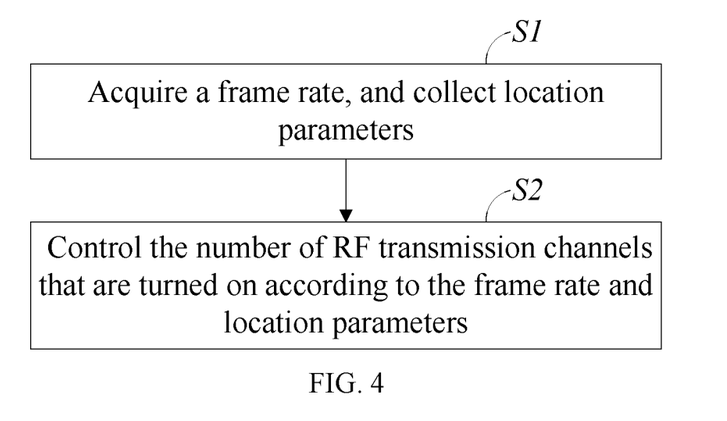
FIG. 4 is a flowchart of a control method for the capsule endoscope according to a second embodiment of the present invention.

In the second embodiment of the present invention, the interacted data further comprises magnetic field signals used to locate the position of the capsule endoscope. Accordingly, as shown in FIG. 4, step S1 further comprises: collecting location parameters of the capsule endoscope, where the location parameters are magnetic field signals collected by the capsule endoscope in real time. Step S2 further comprises: controlling the number of RF transmission channels that are turned on according to the frame rate and location parameters, and the RF transmission channels are also used for transmission of the location parameters.

After the magnetic field signals are transmitted to the data recorder through the RF transmission channels, the data recorder can analyze the transmitted magnetic field signals for solving the orientation of the capsule endoscope and determining the specific position and specific posture of the capsule endoscope.

In a preferred embodiment of the present invention, the current position information of the capsule endoscope is also used to determine whether the collected location parameters of the capsule endoscope are empty. It should be understood that when the position of the capsule endoscope is determined, it can be determined whether magnetic field signals need to be transmitted. If the magnetic field signals need to be transmitted, it is determined that the collected location parameters are not empty, and if the magnetic field signals does not need to be transmitted, it is determined that the collected location parameters are empty.

Figure 5:
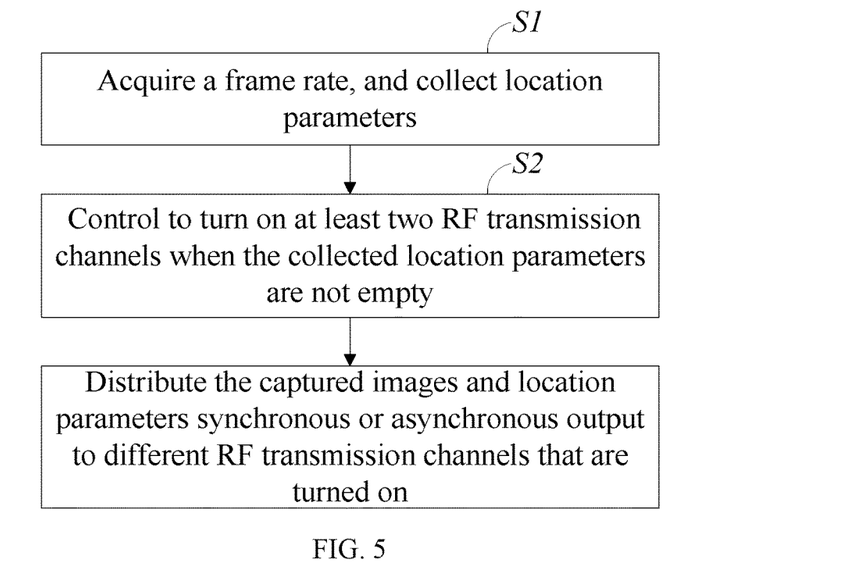
FIG. 5 is a flowchart of a preferred embodiment corresponding to FIG. 4.

In the second embodiment, as shown in FIG. 5, step S2 specifically comprises: if the collected location parameters are not empty, controlling to turn on at least two RF transmission channels; distributing the captured images and location parameters synchronous or asynchronous output to different RF transmission channels that are turned on.

Take the example shown in FIG. 4 as an example: for step S2, the capsule endoscope in the small intestine is taken as an example for detailed introduction. In the small intestine, the capsule endoscope may capture images at a very low frame rate or even stop capturing images, but due to positioning requirements, the magnetic field signals should be interacted in real time. Therefore, the image information and magnetic field signals are distributed to different RF transmission channels that are turned on for synchronous or asynchronous output. In this example, the captured images are distributed to the first RF transmission channel for interaction and the collected magnetic field signals are distributed to the second RF transmission channel for interaction. In this way, the information to be transmitted at low speed transmission and the information to be transmitted at high speed are transmitted through different RF transmission channels so that they do not affect each other. This method can not only achieve the purpose of saving resources, but also ensure the normal operation of equipment.

In a preferred embodiment of the present invention, an improvement on the basis of the second embodiment, step S2 specifically comprises: if the collected location parameters are not empty, and the frame rate is greater than the system preset frame rate, controlling to turn on at least three RF transmission channels; distributing the location parameters to one of the RF transmission channels for output; cross-distributing the captured images to at least other two RF transmission channels for synchronous or asynchronous output.

Figure 6:
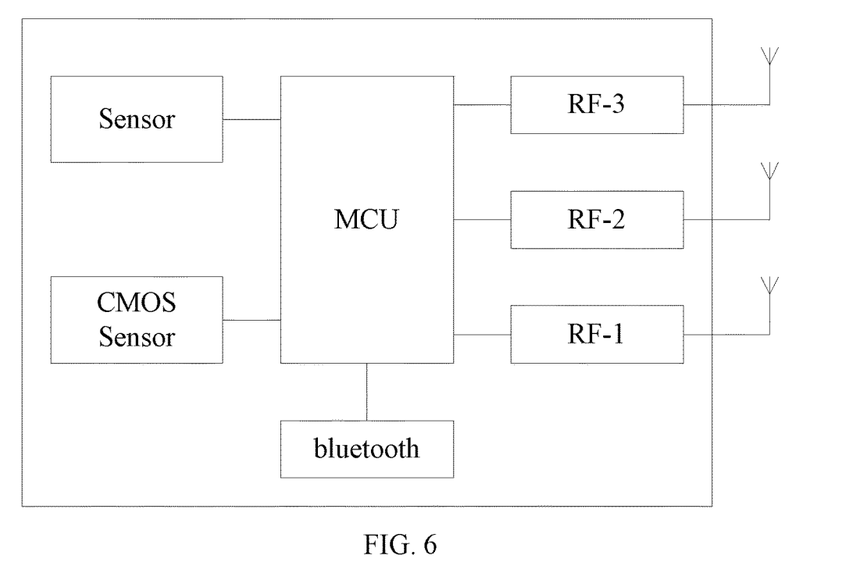
FIG. 6 is a block diagram showing the hardware structure of the capsule endoscope in another specific example of the present invention.

Accordingly, as shown in FIG. 6, the number of the RF modules provided in the capsule endoscope is 3. The three RF modules correspond to three RF transmission channels, and the three RF transmission channels are a first RF transmission channel RF-1, a second RF transmission channel RF-2 and a third RF transmission channel RF-3. Taking the capsule endoscope in the stomach as an example, in this example, the collected frame rate is greater than the system preset frame rate, and the collected magnetic field signals are not empty. At this point, the captured images are distributed to the first RF transmission channel RF-1 and the second transmission channel RF-2 for cross and synchronous output, and the collected magnetic signals are output through the third RF transmission channel RF-3. Therefore, both the high-rate transmission of images and the high-rate transmission of magnetic signals can be guaranteed. In addition, in other embodiments of the present invention, more RF modules can also be provided, and more RF transmission channels can be allocated for image transmission when the frame rate is greater than the system preset frame rate, which cannot be further described here.

In a third embodiment of the present invention, the interacted information may also comprise other control parameters, such as working parameters obtained through at least one of an acceleration sensor, a gyroscope, a pH sensor, a pressure sensor, and a temperature sensor. Accordingly, in the third embodiment, on the basis of said embodiments, the RF transmission channels are also used to transmit control parameters. Step S1 also comprises: collecting control parameters of the capsule endoscope, and step S2 also comprises: distributing the captured images and at least one control parameter to the different RF transmission channels that are turned on for synchronous or asynchronous output.

Accordingly, as shown in FIG. 6, when the collected magnetic field signals and control parameters are not empty, the captured images are interacted through the first RF transmission channel RF-1, the collected magnetic field signals are distributed to the second RF transmission channel RF-2 for interaction and the control parameters are distributed to the third RF transmission channel RF-3 for interaction. Also, the captured images can be interacted through the first RF transmission channel RF-1 and the second RF transmission channel RF-2, and the collected magnetic field signals and control parameters can all be distributed to the third RF transmission channel RF-3 for interaction. In this method, a plurality of RF modules share the transmission of various parameters and improve transmission efficiency.

Under normal circumstances, the capsule endoscope needs to be discharged from the subject after the work is completed. However, the existing examination method requires the subject to go to the hospital and have a scanning on his body with a special device, which is quite inconvenient. In a preferred embodiment of the present invention, a RF broadcast module is added to the capsule endoscope. The RF broadcast module is, for example, a Bluetooth module. When the capsule endoscope is in the subject, the Bluetooth module is turned on and broadcast is performed through the Bluetooth module. Then, the broadcast information can be identified by any smart device outside the subject, such as a mobile phone to determine whether the capsule endoscope is discharged from the subject. After swallowing the capsule endoscope, the subject can check on his own to determine whether the capsule endoscope is discharged from the subject, which is convenient for operation and use.

Preferably, the method further comprises: turning on the Bluetooth module in the capsule endoscope to broadcast after the capsule endoscope receiving that work RF transmission channels are all turned off, where the information carried by the broadcast comprising the unique identification number of the current capsule endoscope; determining whether the capsule endoscope is in a preset position according to the broadcast information. The preset position is, for example, inside or outside the subject. Normally, the position is outside the subject, so that the method can be used to determine whether the capsule endoscope is discharged from the subject, which is convenient for operation and use.

In the specific implementation process of the present invention, when it is identified that the RF transmission channels are all turned off, or with an auxiliary operation by the subject, it can be determined that the capsule endoscope finishes working.

Figure 7:
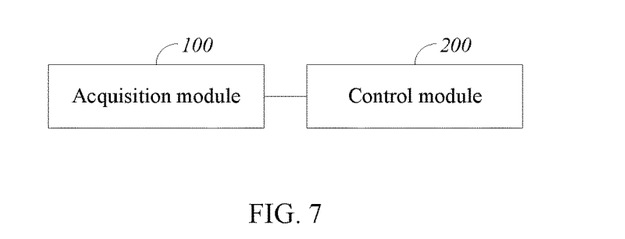
FIG. 7 is a schematic diagram of modules of the control system according to an embodiment of the present invention.

FIG. 7 shows a control system for the capsule endoscope according to the first preferred embodiment of the present invention. The control system comprises an acquisition module 100 and a control module 200.

The acquisition module 100 is used to acquire a frame rate of the capsule endoscope, where the frame rate is the number of frames of images captured by the capsule endoscope per unit time. The control module 200 is used to control the number of RF transmission channels that are turned on according to the frame rate, where the number of RF transmission channels is set to at least two, and the RF transmission channels are used for transmission of the captured images.

In a preferred embodiment of the present invention, the acquisition module 100 acquires the frame rate of the capsule endoscope according to the current position information of the capsule endoscope.

In the specific embodiment of the present invention, the control module 200 is specifically used to: if the frame rate is greater than the system preset frame rate, control to turn on at least two RF transmission channels; cross-distribute the captured images to the RF transmission channels that are turned on for synchronous or asynchronous output.

In a second embodiment of the present invention, the acquisition module 100 is also used to collect location parameters of the capsule endoscope. The location parameters are the magnetic field signals collected by the capsule endoscope in real time. The control module 200 is also used to control the number of RF transmission channels that are turned on according to the frame rate and location parameters, wherein the RF transmission channels are also used for transmission of the location parameters.

In the second embodiment, the acquisition module 100 is also used to determine whether the collected location parameters of the capsule endoscope are empty according to the current position information of the capsule endoscope.

In the second embodiment, the control module 200 is specifically used to: when the collected location parameters are not empty, control to turn on at least two RF transmission channels; distribute the collected images and location parameters to different RF transmission channels that are turned on for synchronous or asynchronous output.

Further, in another implementation of the second embodiment, the control module 200 can also be used to: if the collected location parameters are not empty, and the frame rate is greater than the system preset frame rate, control to turn on at least three RF transmission channels; distributing the location parameters to one of the RF transmission channels that are turned on for output; cross-distributing the collected images to at least other two RF transmission channels that are turned on for synchronous or asynchronous output.

In a third embodiment of the present invention, the interacted information may also comprise other control parameters, such as working parameters obtained through at least one of an acceleration sensor, a gyroscope, a pH sensor, a pressure sensor, and a temperature sensor. Accordingly, in the third embodiment, that is improved on the basis of the first and second embodiments, the RF transmission channels are also used to transmit control parameters; the acquisition module 100 is also used to collect control parameters; the control module 200 is also used to distribute the collected images and at least one control parameter to different RF transmission channels that are turned on for synchronous or asynchronous output.

On the basis of the above three embodiments, the control module 200 is also used to turn on the Bluetooth module in the capsule endoscope to broadcast after the capsule endoscope receiving work RF transmission channels are all turned off. The broadcast information comprises the unique identification number of the current capsule endoscope. The control module 200 is also used to determine whether the capsule endoscope is in the preset position by receiving the broadcast information.

Those skilled in the art can clearly understand that, for the convenience and conciseness of the description, the specific working process of the system described above cannot be repeated as it has been detailed in the foregoing method implementation.

In summary, the control method and control system for the capsule endoscope disclosed in the present invention can adaptively distribute a plurality of radio frequency transmission channels according to the real-time position of the capsule endoscope, and further turn on the radio frequency transmission channels to transmit a plurality of signals synchronously or asynchronously, so that the detection requirements can be met and also the energy consumption can be saved. In addition, by disposing a Bluetooth module, the capsule endoscope can be located to identify whether it is discharged from the subject, and this improves the efficiency of using the capsule endoscope.

For the convenience of description, the device is described in various modules divided by functions separately. When implementing the present invention, the functions of the various modules can be implemented in the same or different software and/or hardware.

In accordance with aspects of the present invention, the control module is executed by one or more processors. The processors are configured to execute a plurality of steps instructed by control module. The module's instructions are retrieved from a memory storage and loaded into the computer processor(s). The processor(s) decode these instructions and carry out the required actions as specified.

The device implementations described above are merely illustrative. The modules described as separate components may or may not be physically separated, and the components displayed as modules may or may not be physical modules, that is, they may be located in one place, or may also be distributed over a plurality of network modules. Some or all of the modules may be selected according to actual needs to achieve the object of the embodiment. It can be understood and implemented by ordinary persons skilled in the art without creative work.

It should be understood that, although the specification is described in terms of embodiments, not every embodiment merely includes an independent technical solution. This narration in the specification is only for clarity. Those skilled in the art should have the specification as a whole, and the technical solutions in each embodiment may also be combined as appropriate to form other embodiments that can be understood by those skilled in the art.

The series of detailed descriptions listed above are only specific descriptions of the feasible embodiments of the present invention, and are not intended to limit the protection scope of the present invention. Any equivalent embodiments or variations made without departing from the technical spirit of the present invention should be included in the protection scope of the present invention.

What is claimed is:

1. A control method for a capsule endoscope, comprising:
acquiring a frame rate of the capsule endoscope, wherein the frame rate is the number of frames of images captured by the capsule endoscope per unit time;
controlling a number of radio frequency transmission channels that are turned on simultaneously according to the frame rate and positioning parameters, by
controlling to turn on at least two radio frequency transmission channels when the frame rate is greater than a system preset frame rate; and
cross-distributing the captured images to the radio frequency transmission channels that are turned on for synchronous or asynchronous output;
wherein the number of radio frequency transmission channels that are simultaneously turned on is at least two, and the radio frequency transmission channels transmit the captured images.

2. The control method of claim 1, further comprising:
collecting location parameters of the capsule endoscope, wherein the location parameters are magnetic field signals collected by the capsule endoscope in real time; and
controlling the number of radio frequency transmission channels that are turned on according to the frame rate and location parameters,
wherein the radio frequency transmission channels transmit the location parameters.

3. The control method of claim 2, wherein the controlling the number of radio frequency transmission channels that are turned on comprises:
determining whether the positioning parameters are empty, wherein the positioning parameters include the location parameters and orientation parameters;
if the positioning parameters are empty, indicating that no positioning request is required;
determining whether the collected location parameters are not empty;
if the collected location parameters are not empty, inferring the reception of a positioning request;
activating at least two radio frequency transmission channels in response to the collected location parameters not being empty, indicating the reception of a positioning request;
distributing the captured images and location parameters for synchronous or asynchronous output to different radio frequency transmission channels that are activated.

4. The control method of claim 3, wherein the controlling the number of radio frequency transmission channels that are turned on comprises:
controlling to turn on at least three radio frequency transmission channels when the collected location parameters are not empty and the frame rate is greater than a system preset frame rate;
distributing the collected location parameters to one of the radio frequency transmission channels for output; and
cross-distributing the captured images to at least two other radio frequency transmission channels for synchronous or asynchronous output.

5. The control method of claim 4, wherein the controlling the number of radio frequency transmission channels that are turned on comprises:
identifying the frame rate of the capsule endoscope, and/or determining whether the collected location parameters are empty according to the current position information of the capsule endoscope.

6. The control method of claim 1, wherein the method further comprises
collecting control parameters of the capsule endoscope, wherein the control parameters are working parameters obtained by at least one of acceleration sensor, a gyroscope, a pH sensor, a pressure sensor and a temperature sensor; and
distributing the captured images and at least one control parameter to different radio frequency transmission channels that are turned on for synchronous or asynchronous output when the collected control parameters are not empty.

7. The control method of claim 1, wherein the method further comprises:
turning on a Bluetooth module of the capsule endoscope to broadcast information after the capsule endoscope finishes working, wherein the broadcast information comprises a unique identification number of the current capsule endoscope;
determining whether the capsule endoscope is in a preset position according to the broadcast information.

8. A control system for a capsule endoscope, comprising:
one or more computer processors configured to:
acquire a frame rate of the capsule endoscope, wherein the frame rate is the number of frames of images captured by the capsule endoscope per unit time;
control the number of radio frequency transmission channels that are turned on according to the frame rate, by
controlling to turn on at least two radio frequency transmission channels when the frame rate is greater than a system preset frame rate; and
cross-distributing the captured images to the radio frequency transmission channels that are turned on for synchronous or asynchronous output;
wherein the number of radio frequency transmission channels that are turned on is at least two, and the radio frequency transmission channels transmit the captured images.

9. The control system of claim 8, wherein the one or more computer processors is further configured to:
collect location parameters of the capsule endo scope, wherein the location parameters are magnetic field signals collected by the capsule endoscope in real time; and
control the number of radio frequency transmission channels that are turned on according to the frame rate and location parameters, wherein the radio frequency transmission channels transmit the location parameters.

10. The control system of claim 9, wherein the one or more computer processors is further configured to:
control to turn on at least two radio frequency transmission channels when the collected location parameters are not empty;

distribute the captured images and location parameters for synchronous or asynchronous output to different radio frequency transmission channels that are turned on.

11. The control system of claim 9, wherein the one or more computer processors is further configured to:
control to turn on at least three radio frequency transmission channels when the collected location parameters are not empty and the frame rate is greater than a system preset frame rate;
distribute the collected location parameters to one of the radio frequency transmission channels for output;
cross-distribute the captured images to at least two other radio frequency transmission channels for synchronous or asynchronous output.

12. The control system of claim 9, wherein the one or more computer processors is further configured to:
identify the frame rate of the capsule endoscope, and/or determine whether the collected location parameters are empty according to the current position information of the capsule endoscope.

13. The control system of claim 8, wherein
the one or more computer processors is further configured to collect control parameters of the capsule endoscope, wherein the control parameters are working parameters obtained by at least one of acceleration sensors, a gyroscope, a pH sensor, a pressure sensor, and a temperature sensor;
the control module is configured to distribute the captured images and at least one control parameter to different radio frequency transmission channels that are turned on for synchronous or asynchronous output when the collected control parameters are not empty.

14. The control system of claim 8, wherein the one or more computer processors is further configured to:
turn on a Bluetooth module of the capsule endoscope to broadcast information after the capsule endoscope finishes working, wherein the broadcast information comprises a unique identification number of the current capsule endoscope; and
determine whether the capsule endoscope is in a preset position according to the broadcast information.

\* \* \* \* \*